United States Patent [19]

Rising

[11] Patent Number: 5,795,461
[45] Date of Patent: Aug. 18, 1998

US005795461A

[54] ELECTRODE SYSTEM FOR MONITORING CORROSION

[76] Inventor: Brandt A. Rising, 98 S. Bay Ave., Brightwaters, N.Y. 11718

[21] Appl. No.: 623,318

[22] Filed: Mar. 26, 1996

[51] Int. Cl.[6] .................................................. G01N 27/26
[52] U.S. Cl. ..................... 205/775.5; 205/777; 324/71.2; 204/404
[58] Field of Search .......................... 204/404; 205/775.5, 205/777; 324/71.2, 425

[56] References Cited

U.S. PATENT DOCUMENTS

| | | | |
|---|---|---|---|
| 4,755,267 | 7/1988 | Saunders | 205/726 |
| 4,806,850 | 2/1989 | Saumade et al. | 205/775.5 |
| 5,529,668 | 6/1996 | Hall | 205/776.5 |
| 5,609,740 | 3/1997 | Hasegawa et al. | 204/400 |

OTHER PUBLICATIONS

J. O'M. Bockris, "Modern Electrochemistry–vol. 2", Plenum/Rosetta (1973), pp. 1269–1273.

*Primary Examiner*—Nam Nguyen
*Attorney, Agent, or Firm*—Wolf, Greenfield & Sacks, P.C.

[57] ABSTRACT

An electrode system for monitoring potentials between electrodes that includes a structure having a surface, a first electrode, a second electrode, an electrolyte, and a monitor to measure the potentials between the first and second electrodes. The first electrode is connected to the surface of the structure. The second electrode and surface of the structure are each in direct physical contact with the electrolyte so that a potential exists between the first and second electrodes. In certain embodiments, the electrode system may further include a reference electrode that is in physical contact with the electrolyte and physically isolated from the first and second electrodes so that a potential exists between the reference, first, and second electrodes. Optionally, the electrode system further includes an apparatus for measuring a background change in the potentials between electrodes and compensating for this background change. The present invention also provides a method of monitoring corrosion of the surface of a structure by monitoring potentials between electrodes.

20 Claims, 6 Drawing Sheets

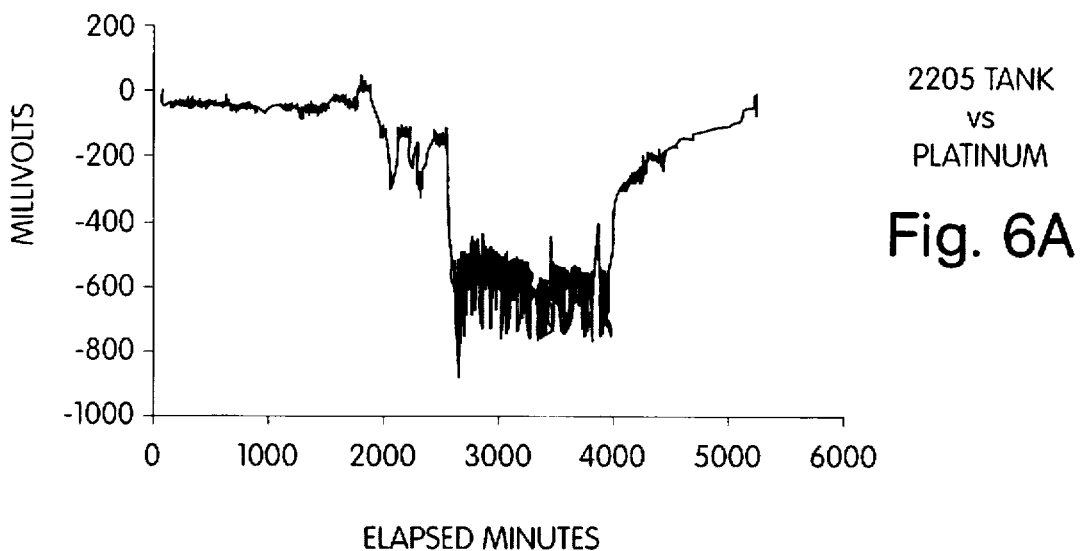
Fig. 6A — 2205 TANK vs PLATINUM
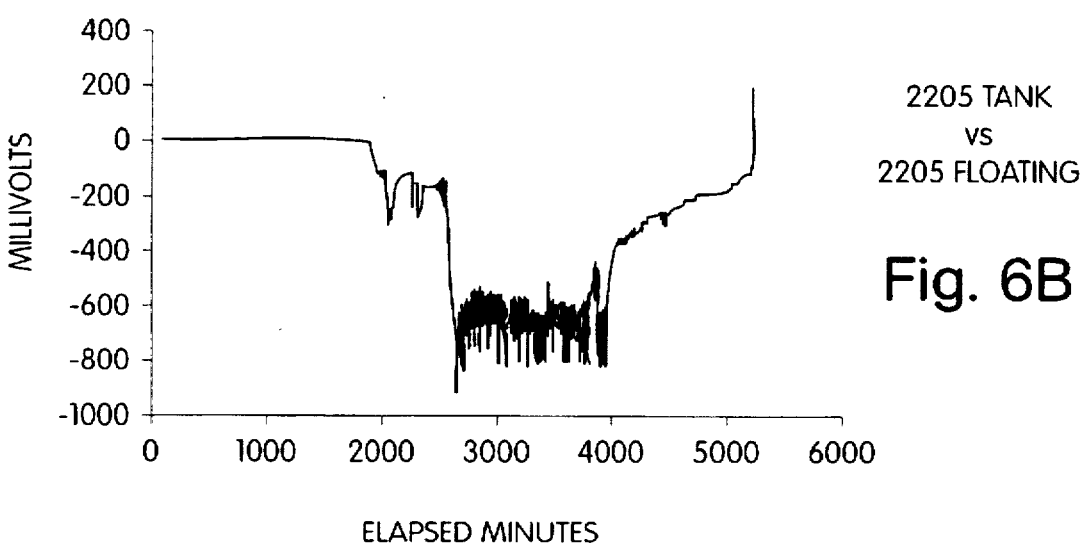
Fig. 6B — 2205 TANK vs 2205 FLOATING
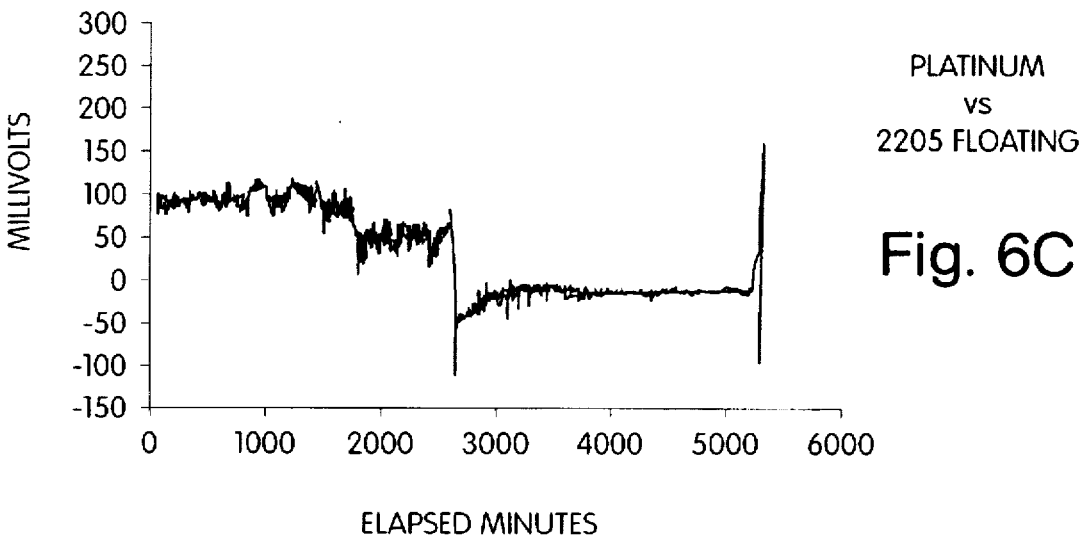
Fig. 6C — PLATINUM vs 2205 FLOATING

ELECTRODE SYSTEM FOR MONITORING CORROSION

BACKGROUND OF THE INVENTION

1. Field of the Invention

The present invention relates generally to electrode systems for monitoring potentials between electrodes, and more specifically to such systems which are capable of monitoring and determining corrosion of metallic materials.

2. Discussion of the Related Art

Corrosion of a metallic material may occur whenever the metallic material is in contact with an electrolyte. There are essentially two processes by which such corrosion occurs. In one process, referred to as electrolyte-induced corrosion, a metallic material undergoes corrosion as the result of chemistry between the metallic material and the electrolyte. The chemical processes which occur in electrolyte-induced corrosion can be explained by standard theories of chemical kinetics and thermodynamics. In the other process, corrosion of a metallic material results from exposure of the metallic material to an external electrical or magnetic force while the metallic material is in contact with an electrolyte. These external electrical or magnetic forces are limited only in that they change the surface potential of the metallic material and include induced currents, DC currents, and AC currents.

Regardless of the cause, it is often desirable to eliminate or at least monitor such corrosion of a metallic material for health, environmental, or financial reasons. For example, copper tubing is used extensively in household plumbing to transport water which is used for cleaning and human consumption. After exposure to the water for an extended period of time, the copper tube may corrode and ultimately form leaks, resulting in potentially significant property damage and rendering the tubing useless. The corrosion of the copper tubing may result from chemistry between the water and the tubing, or the corrosion may occur due to exposure of the tubing to external electrical or magnetic forces. In some cases, both corrosion processes may occur.

Corrosion of various storage tanks can also be a problem. A variety of electrolytes including corrosive chemicals, such as acids, are commonly stored in tanks made of metallic materials. With time, corrosion of the interior of the tank can result in dissolution of tank metals or formation of a sludge composed of the corroded metal and electrolyte components. When storing chemicals, this dissolution of metal can act as an impurity that reduces the utility of the chemical. In addition, if the corrosion is active for a long time, holes may form in storage tanks due to corrosion of the tank interior. Such hole formation allows the electrolyte to escape the tank, resulting in a hazardous situation, an expensive clean up, and loss of the chemical stored in the tank. For fixed storage tanks, hole formation may cause long term exposure of the environment to the electrolyte, resulting in potential environmental problems. Corrosion of storage tanks may be caused by chemistry between the tank and electrolytes contacting the tank or external electrical or magnetic forces may cause the storage tanks to corrode. For certain storage tank systems, corrosion may be due to both external electrical or magnetic influences and chemistry between the tank and the electrolyte.

In the shipping industry, electrolytes, such as corrosive chemicals, are transported in metallic containers that are integral parts of seagoing vessels. It is desirable to prevent tank corrosion because replacing the tanks is expensive and time consuming. In addition, such corrosion results in the loss of cargo quality. Corrosion of the tanks may result from chemistry between the tank and electrolytes contacting the tank, such as salt water and the electrolyte stored within the tank, or corrosion may occur due to external electrical or magnetic forces to which the tanks are exposed. Alternatively, both types of corrosion processes may occur.

Systems designed to monitor and eliminate corrosion of metallic materials are known, but these systems are relatively expensive and can require considerable time and effort for installation and maintenance. Furthermore, known corrosion detection systems are incapable of determining whether the corrosion is caused by an electrolyte or an external electrical or magnetic force to which the metallic material is exposed. Since, in many cases, it is advantageous to delineate between these corrosion processes prior to the purchase and installation of a corrosion prevention system in order to ensure that the problem is solved and that it is solved in the easiest and least expensive manner, there is a need for a method and apparatus to provide this information. In particular, it is desirable to provide an electrode system that is capable of monitoring corrosion of metallic materials and determining the corrosion process that is occurring.

SUMMARY OF THE INVENTION

In accordance with the above, this invention provides an electrode system that can monitor corrosion of metallic materials and determine the process that is causing such corrosion.

In one illustrative embodiment, the present invention comprises an electrode system for monitoring corrosion of a surface of a structure formed of a metallic material. The electrode system includes a first electrode, a second electrode, an electrolyte, and a monitor to measure the potential between the electrodes. The first electrode is connected to the surface of the structure, and the electrolyte is in direct physical contact with the surface of the structure and the second electrode. For a more specific embodiment, the electrode system further includes a reference electrode formed of platinum, the structure is in the shape of a container, and the electrolyte is an electrolytic solution.

The invention also provides a method of monitoring corrosion associated with the surface of a structure formed of a metallic material. An electrolytic solution is in contact with the surface of the structure. The method includes: connecting a first electrode to the interior surface of the structure; physically contacting a second electrode with the electrolytic solution; and physically contacting a third electrode with the electrolytic solution. The electrodes are each physically isolated from each other so that potentials exist between each electrode. The method further includes the steps of measuring a first potential between two of the electrodes and measuring a second potential between two other electrodes. Optionally, the method may include a step of measuring a third potential between two electrodes which is different than either the first or second potentials.

BRIEF DESCRIPTION OF THE DRAWINGS

The objects, advantages and features of the present invention will be more clearly appreciated from the following detailed description when taken in conjunction with the accompanying drawings, in which:

FIGS. 6A–6C show the potential as a function of time for a type 2205 stainless steel ship tank holding sulphuric acid according to one embodiment of the present invention.

DETAILED DESCRIPTION

Figure 1:
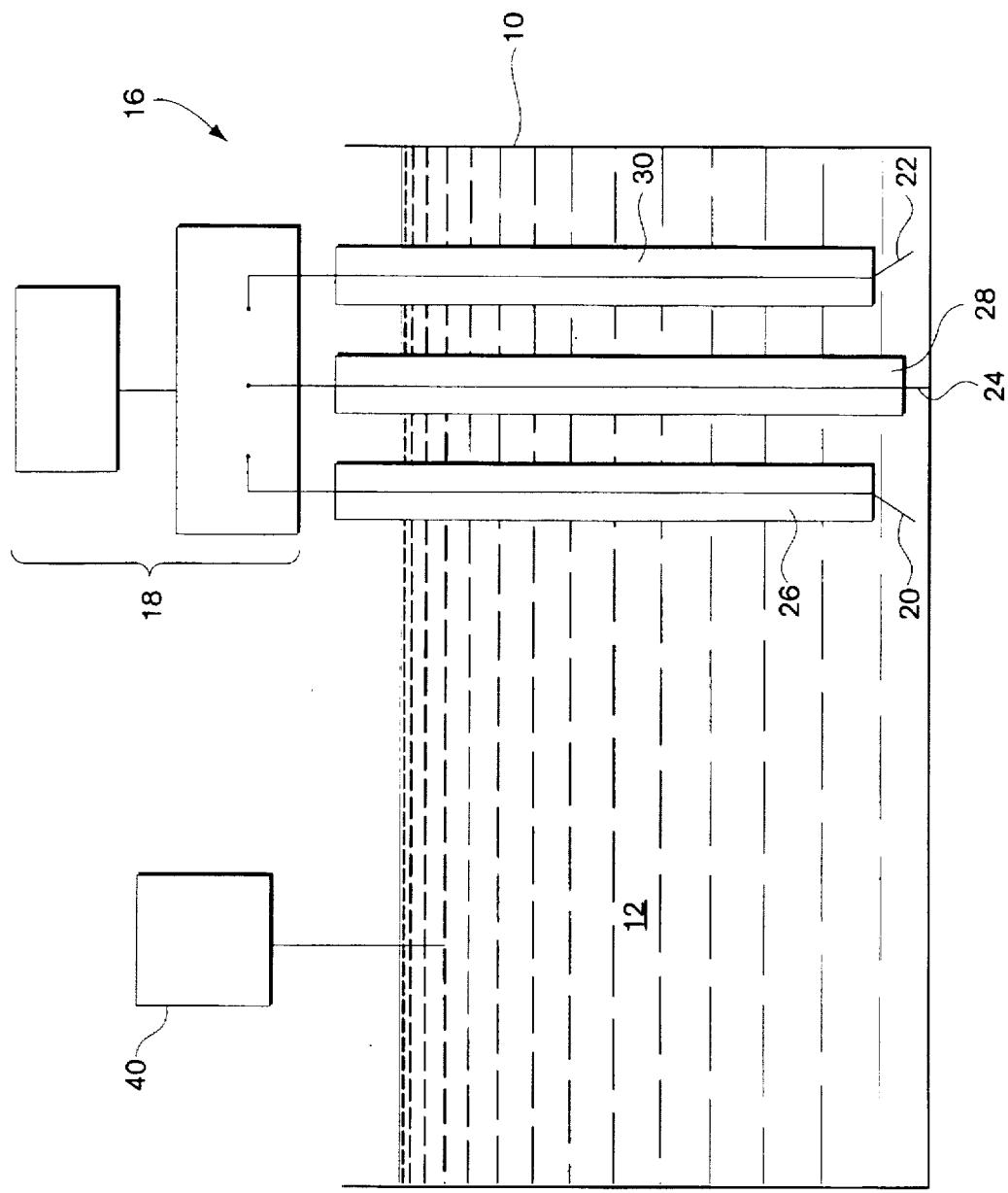
FIG. 1 is a schematic representation of one embodiment of an electrode system according to the present invention.

FIG. 1 depicts one embodiment of an electrode system in accordance with the present invention. In FIG. 1, an electrolyte 12 is in contact with the interior of a metallic material 10. Electrode system 16 includes data collection and analysis electronics 18, reference electrode 20, floating electrode 22 and metallic material electrode 24. Apparatus 16 is arranged such that electrodes 20, 22, and 24 are each in contact with electrolyte 12. In addition, electrodes 20, 22, and 24 each are covered by a protective cover 26, 28, and 30, respectively. Electrodes 22 and 24 are formed of the same metallic material and electrode 24 is electrically connected to metallic material 10.

An "electrolyte" as used herein refers to a nonmetallic fluid or semi-solid that is sufficiently conductive to permit two dissimilar metallic materials to establish a potential difference when the dissimilar metals are each contacting the electrolyte. Typically, liquid electrolytes are ionic solutions having salts dissolved therein. An illustrative and nonlimiting list of liquid electrolytes includes tap water, sea water, sulphuric acid, boric acid, and phosphoric acid. Other electrolytes appropriate for use with the present invention will be apparent to those skilled in the art.

"Metallic material" as used herein denotes a metal, an alloy, or a combination thereof. A metallic material may be a solid, semi-solid, or liquid. Typically, a metallic material is a solid. In certain embodiments, metallic material 10 may be a tank of a sea going vessel formed from a stainless steel, such as type 2205 stainless steel. In some embodiments, metallic material 10 may be a tube or pipe formed from copper.

As used herein, the term "corrosion" refers to a chemical change in a metallic material, such as material 10, accompanied by a dissolution of the metal or formation of a metal compound which results in a change in the surface potential of the material. Often, such corrosion is accompanied by a decrease in a useful property of the metallic material. For example, corrosion may decrease the mechanical integrity of the metallic material. Furthermore, corrosion of the metallic material may result in the introduction of impurities into an electrolyte.

An "electrode" as used herein denotes a structure having an exterior which is at least partially formed of a metallic material. In some embodiments, an electrode may have an interior which is not a metallic material and an exterior which is partially or fully made of a metallic material. For such embodiments, the metallic material may be dip coated, spray coated, vapor deposited, or otherwise bonded to the interior.

With reference to FIG. 1, the present invention provides electrode system 16 which is capable of determining whether corrosion of metallic material 10 is the result of chemistry between electrolyte 12 and material 10 or influences including but not limited to external electrical or magnetic influences to which material 10 is exposed. One operational theory of electrode system 16 is as follows. Because electrodes 22 and 24 are formed of the same metallic material, electrodes 22 and 24 undergo the same chemistry with electrolyte 12. Thus, any corrosion induced by electrolyte 12 will not result in a difference in potential between electrodes 22 and 24. If electrode system 16 is constructed such that floating electrode 22 is not susceptible to external electrical or magnetic influences on metallic material 10, electrode 22 does not undergo any change induced by these external electrical or magnetic forces. However, the surface potential of metallic material 10 may change, resulting in a change in the potential of metallic material electrode 24. As a result, a change in the potential between electrodes 22 and 24 demonstrates possible corrosion of metallic material 10 which is caused by external electrical or magnetic forces to which material 10 is exposed and from which floating electrode 22 is isolated. Therefore, to delineate between electrolyte-induced corrosion of material 10 and corrosion of material 10 caused by external electrical or magnetic influences, system 16 should be arranged such that floating electrode 22 is isolated from these external electrical or magnetic influences. Typically, this is accomplished by metallic material 10 shielding the external electrical or magnetic influence.

Figure 2A:
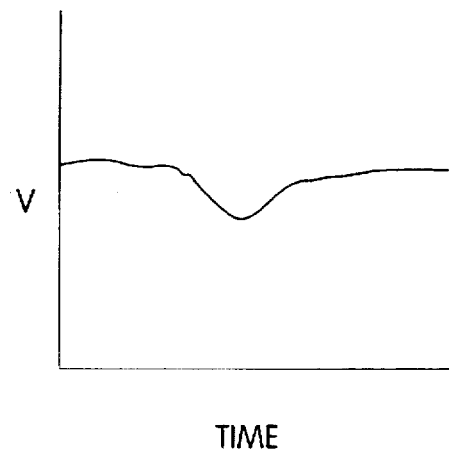
FIGS. 2A–2C are graphs of the potential between electrodes as a function of time for one embodiment of an electrode system according to the present invention, wherein a metallic material undergoes electrolyte-induced corrosion.
Figure 2B:
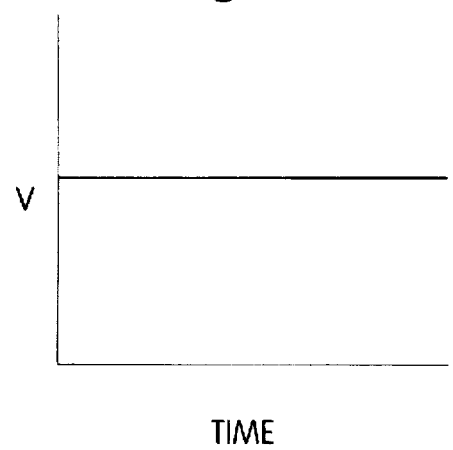
Figure 2C:
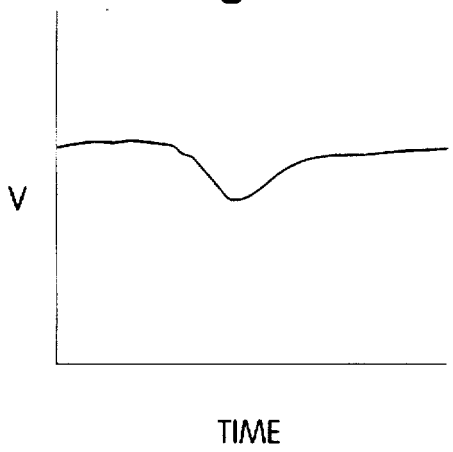

FIGS. 2A–2C are exemplary graphical representations of data produced by an electrode system in accordance with the present invention. FIGS. 2A–2C, respectively, show the potential difference between electrodes 20 and 24, 22 and 24, and 20 and 22 as a function of time for a situation in which corrosion of metallic material 10 results from chemistry between material 10 and electrolyte 12. Under these circumstances, as shown in FIGS. 2A and 2C, the change in potential between metallic material electrode 24 and reference electrode 20 is the same as the change in potential between floating electrode 22 and reference electrode 20. In addition, FIG. 2B shows that the potential between floating electrode 22 and metallic material electrode 24 does not change as a function of time.

Figure 3A:
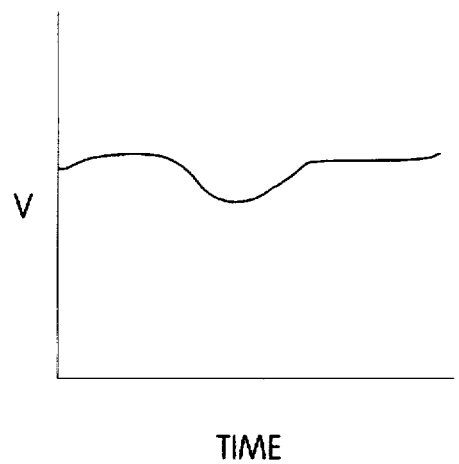
FIGS. 3A–3C are graphs of the potential between electrodes as a function of time for one embodiment of an electrode system according to the present invention, wherein a metallic material undergoes corrosion which is induced by an external electrical or magnetic force to which the metallic material is exposed.
Figure 3B:
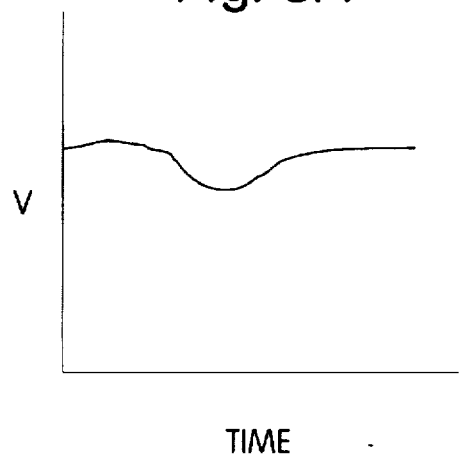
Figure 3C:
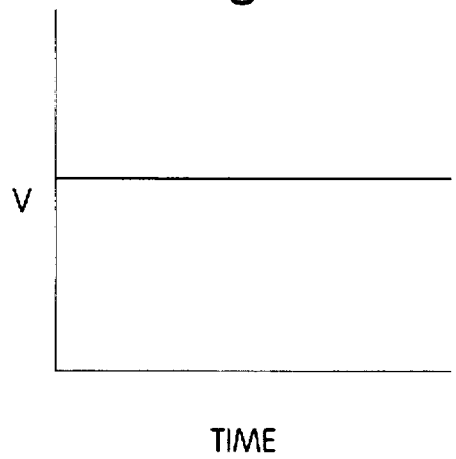

FIGS. 3A–3C depict another set of exemplary graphical representations for data produced by an electrode system in accordance with the present invention. FIGS. 3A–3C show, respectively, the potential between electrodes 20 and 24, 22 and 24, and 20 and 22 as a function of time for conditions under which metallic material 10 undergoes corrosion due to external electrical or magnetic influences to which material 10 is exposed. FIG. 3A shows that the potential between metallic material electrode 24 and reference electrode 20 changes as a function of time, indicating corrosion of metallic material 10. Furthermore, as shown in FIG. 3B, the potential between floating electrode 22 and metallic material electrode 24 changes with time. Thus, floating electrode 22 is not undergoing corrosion. Moreover, FIG. 3C demonstrates that the potential between reference electrode 20 and floating electrode 22 does not change as a function of time, providing additional evidence that metallic material 10 is undergoing corrosion and that floating electrode 22 is not.

It is to be noted that, while FIGS. 2A–2C and FIGS. 3A–3C show relatively sharp changes in the potentials between electrodes as a function of time, in many embodiments of the present invention the change in potentials between electrodes may be more gradual. In addition, the change in the potentials between electrodes may be relatively small. For either case, the change in the potential between electrodes 20, 22 and 24 may be difficult to distinguish from background noise. For such measurements, data collection and analysis electronics 18 should be sensitive enough to distinguish the change in the potential between electrodes 20, 22 and 24 from any background noise.

Although depicted in FIG. 1 as a container, metallic material 10 may be in any shape so long as it is capable of contacting electrolytes 12. For example, material 10 may be in the form of a tank of a ship, a tube, a conductive laboratory container, or a surface which may, for example, form a part of a separating barrier for at least one electrolyte. Other shapes of metallic material 10 which are in accordance with the present invention will be apparent to those skilled in the art.

Reference electrode 20 should be formed of a material which does not interfere with the operation of electrode system 16 and which provides a stable and reproducible potential when in contact with electrolyte 12 during the course of a corrosion monitoring and determination experiment. By "stable and reproducible potential" it is herein meant to refer to a potential that does not change without a change in the system so that the potential may be used as a comparative reference potential. Accordingly, materials appropriate for use in constructing electrode 20 depend upon the chemical composition of electrolyte 12. Such materials are known to those skilled in the art and are intended to be within the scope of the present invention. For example, if electrolyte 12 is sulfuric acid, reference electrode 20 may comprise platinum or gold. In some embodiments, reference electrode 20 may be a silver—silver chloride electrode, a mercury—mercury chloride electrode or another composite system electrode. As known to those skilled in the art, for such embodiments, electrode 20 may include a working electrolyte and a membrane, small hole, or double junction which allows a small, controlled leak of the working electrolyte into electrolyte 12 so that electrical contact is established between electrolyte 12 and electrode 20. In a preferred embodiment, electrode 20 is formed of a single, solid metal.

According to the present invention, floating electrode 22 serves to monitor the effect of any external electrical or magnetic influences on metallic material 10. Accordingly, electrode 22 where exposed to electrolyte 12, must be formed of the same material as metallic material 10. In addition, electrode 22 should be physically located such that electrode 22 is not susceptible to external electrical or magnetic forces which change the surface potential of metallic material 10. Usually, floating electrode 22 is shielded from the external electrical or magnetic influences by material 10.

Metallic material electrode 24 serves as an electrical link between metallic material 10 and corrosion monitoring apparatus 16, and electrode 24 should demonstrate any change in the surface potential of metallic material 10 (i.e., electrode 24 should be at the same potential as the surface of material 10). Therefore, electrode 24 can be connected to metallic material 10 using any method, such as welding or mechanically attachment, which allows electrode 24 and material 10 to be at the same potential. In addition, since electrode 24 serves primarily as an electrical link between material 10 and apparatus 16, electrode 24 must be formed from the same material as metallic material 10 at points of contact between electrode 24 and electrolyte 12. Moreover, although shown in FIG. 1 as being in physical contact with electrolyte 12, it is not necessary for electrode 24 to be in physical contact with electrolyte 12.

Electrode covers 26, 28, and 30 should be formed of a material which is capable of forming a seal to isolate the electrical connection between a metallic material contained therein, such as a wire or an electrode, and the electrolyte. Furthermore, covers 26, 28, and 30 should be designed to allow electrolyte 12 to be in contact with only a predetermined portion of electrodes 20, 22, and 24, respectively. In addition, covers 26, 28, and 30 should be formed of an electrically insulative, nonmetallic material. Covers 26, 28, and 30 may be directly sealed to electrodes 20, 22, and 24, respectively. Alternatively, covers 26, 28, and 30 may be tube-like structures which contain wires or cables of less expensive and/or more readily available metallic materials, such as copper. For such embodiments, covers 26, 28, and 30 allow for a reduction in the size of electrodes 20, 22, and 24, decreasing the cost associated with electrode system 16. In one embodiment, covers 26, 28, and 30 are formed from Teflon. Other structures and materials appropriate for use as electrode covers 26, 28 and 30 will be apparent to those skilled in the art. In certain embodiments, any or all of electrodes 20, 22, and 24 may not include an electrode cover.

Although depicted in FIG. 1 as being contained within metallic material 10, in some embodiments a portion of the wire or cable located within covers 26, 28, or 30 as well as covers 26, 28, and 30 themselves may extend outside the exterior of metallic metal 10. For such embodiments, since covers 26, 28, and 30 may not shield this portion of the wire or cable from external electrical or magnetic influences, the portion of the wire or cable located outside the exterior of material 10 may be exposed to external electrical or magnetic influences that can change the surface potential of the wire or cable, resulting in inaccurate measurements of the surface potential of material 10. Therefore, for portions of the wire or cable located outside the exterior of material 10, a coaxial wire or a cable with a metal conduit shielding should be used to shield any external electrical or magnetic influences.

Data collection and electronics apparatus 18 is designed to determine the potential between each of electrodes 20, 22, and 24. Hence, apparatus 18 preferably has a high impedance. In addition to measuring the potential between electrodes 20, 22, and 24, apparatus 18 may be capable of recording these potentials. In certain embodiments, apparatus 18 may also be capable of storing this information on a computer. In some embodiments, apparatus 18 is capable of plotting the potentials between electrodes 20, 22, and 24 as a function of time in the form of a hard copy or on a monitor.

Figure 4:
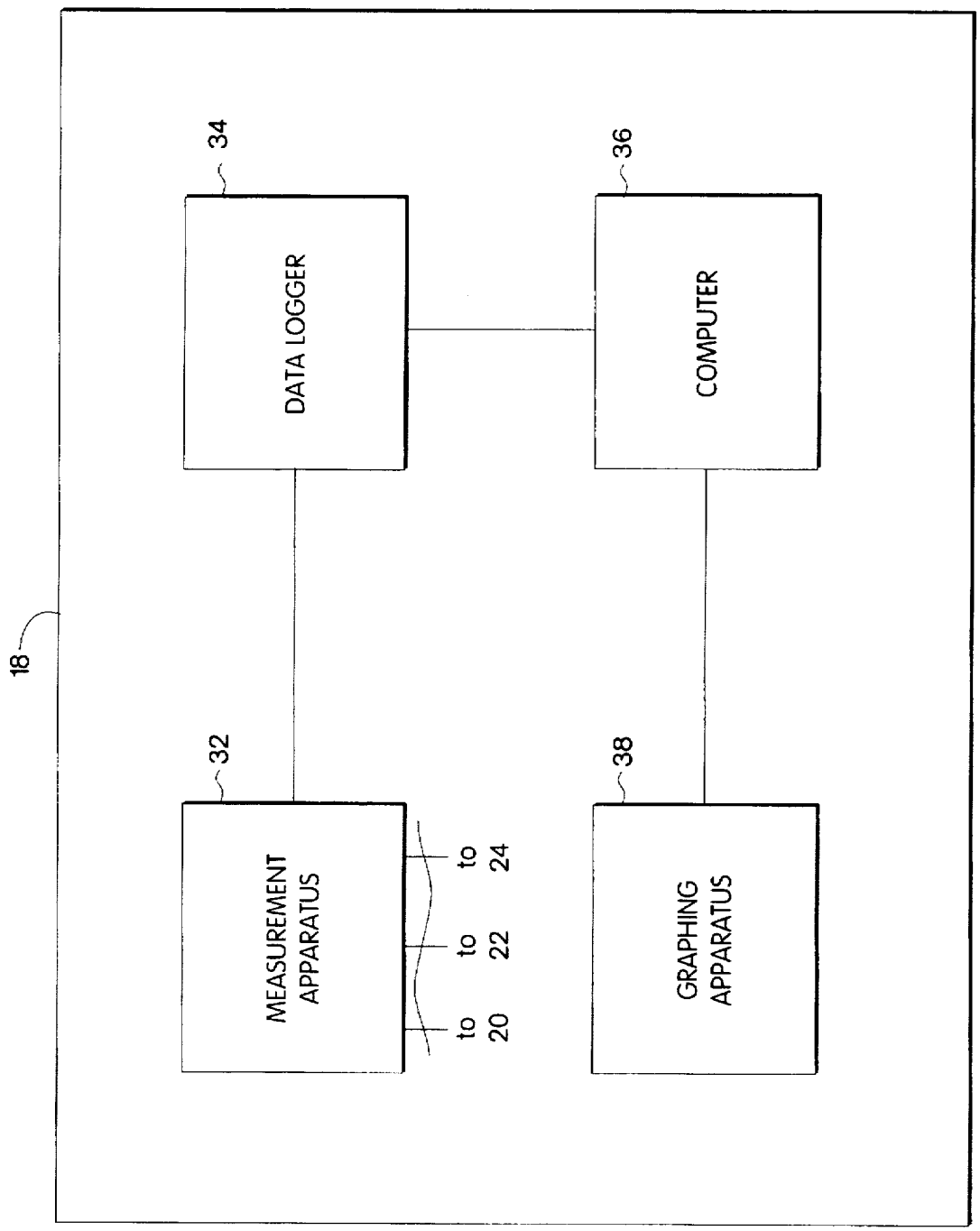
FIG. 4 is a block diagram of the data collection and analysis electronics associated with one embodiment of the present invention.

FIG. 4 is a block diagram for one embodiment of apparatus 18 according to the present invention. As shown in FIG. 4, apparatus 18 includes measurement apparatus 32 which is electrically connected to each of electrodes 20, 22, and 24 while maintaining a high impedance between electrodes 20, 22, and 24. Typically, apparatus 32 is a high impedance volt meter. However, other appropriate devices for apparatus 32 are known to those of ordinary skill in the art.

Measurement apparatus 32 outputs a signal to data logger 34 which preferably records the potentials of electrodes 20, 22, and 24 at short intervals relative to the time scale of the corrosion measurement and detection experiment. For embodiments in which the experiment takes place over the course of weeks, data logger 34 may record the potentials of electrodes 20, 22, and 24 at intervals on the order of one minute.

Computer 36 accepts the output of data logger 34. Computer 36 may store this information in memory and/or may output this information to graphing apparatus 38. In some embodiments, computer 36 includes a monitor on which the output of data logger 34 is plotted in the form of a graph showing the potential between electrode 20, 22, and 24 as a function of time.

Graphing apparatus 38 may be any apparatus capable of taking the output of computer 36 and plotting it in the form of a potential between electrodes versus time. For example, graphing apparatus 38 is an X-Y plotter or an equivalent device. The output of data logger 34 may also be sent directly to graphing apparatus 38, particularly for embodiments where data collection and analysis apparatus 18 may not include computer 36.

Under certain circumstances, the relative potential of a metallic material may change without corrosion of the metallic material occurring due to the non-uniform application of one or more alternative external influences which are a non-electrical and/or non-magnetic external influence. Such changes in the relative potential of a metallic material are herein referred to as "background changes in the potential." These background changes in the relative potential occur if the alternative external influence is applied in a non-uniform fashion to material 10 and/or electrodes 20, 22, and 24 such that each of these electrodes does not undergo a change in relative potential due to the alternative external influence. For example, an alternative external influence may only change the relative surface potential of material 10, and, therefore the relative potential of electrode 24 without changing the relative potentials of electrodes 20 and 22. In this case, the potential between electrode 24 and electrode 20 as well as the potential between electrode 24 and electrode 22 would change while the potential between electrodes 20 and 22 would not change. As a result, a possible false indication of corrosion of material 10 may be indicated. It is to be noted that, if such an alternative external influence is applied in a uniform manner to each of electrodes 20, 22, and 24, a change in the relative potentials between these electrodes may be a true indication of corrosion.

A further complication can arise if an alternative external influence is applied in a non-uniform fashion, and the alternative external influence induces corrosion of a metallic material. For example, since the surface potential of a metallic material depends upon the temperature of the material, a variation in the temperature of a metallic material can result in a change in the relative surface potential of the metallic material. If the temperature of metallic material 10 is changed the change in the relative surface potential of material 10 will cause the relative potential of electrode 24 to change. As a result, if the temperature of electrodes 20 and 22 are not changed in a similar fashion to metallic material 10 (i.e., the alternative external influence is non-uniformly applied), the change in the potential between electrode 24 and electrodes 20 and 22 may be due solely to the change in the temperature of electrode 24. Alternatively, the change in the temperature of material 10 may actually induce corrosion of metallic material 10 so that the change in the relative potential between electrode 24 and electrodes 20 and 22 may, at least in part, be due to corrosion of material 10. A uniform change in the temperature of material 10 and electrodes 20, 22 and 24 may induce corrosion, stop corrosion or have no effect on corrosion of the material 10. However, if such a uniform change in the temperature of these components results in a change in the relative potential between electrodes 20, 22, and 24, this change in the relative potentials is an indication that corrosion may be occurring.

In one embodiment, metallic material 10 may be a copper tube for household plumbing. As water flows through material 10, the temperature of material 10 may change, causing a change in the relative potential of material 10. However, depending upon the flow rate of the water and the relative heat capacities of material 10 and electrodes 20, 22, and 24, the change in temperature of material 10 may be different than the change in temperature of one or more of electrodes 20, 22, and 24. The resulting change in the relative potentials of electrodes 20, 22, and 24 may, therefore, result in an indication of a potential change and a possible false indication of corrosion of a metallic material. In contrast, however, the non-uniform change in the temperature of these elements may actually result in corrosion. In this case, the change in the relative potentials of electrodes 20, 22, and 24 may, at least in part, be due to corrosion. Hence, a change in the value of these parameters can lead to a misinterpretation regarding the detection of corrosion of a metallic material. Thus, for this embodiment, correction device 40 should be capable of monitoring the temperatures of material 10 and electrodes 20, 22,and 24. Such a temperature monitoring device may be, for example, a thermocouple or a thermistor. While temperature has been used as an example of an alternative external influence capable of changing the surface potential of a metallic material without inducing corrosion, other such external influences will be apparent to those of ordinary skill in the art. It is intended that the present invention include embodiments of device 40 that are suited to correct for any change in the surface potential that results from such non-electrical or non-magnetic external influences.

Figure 5:
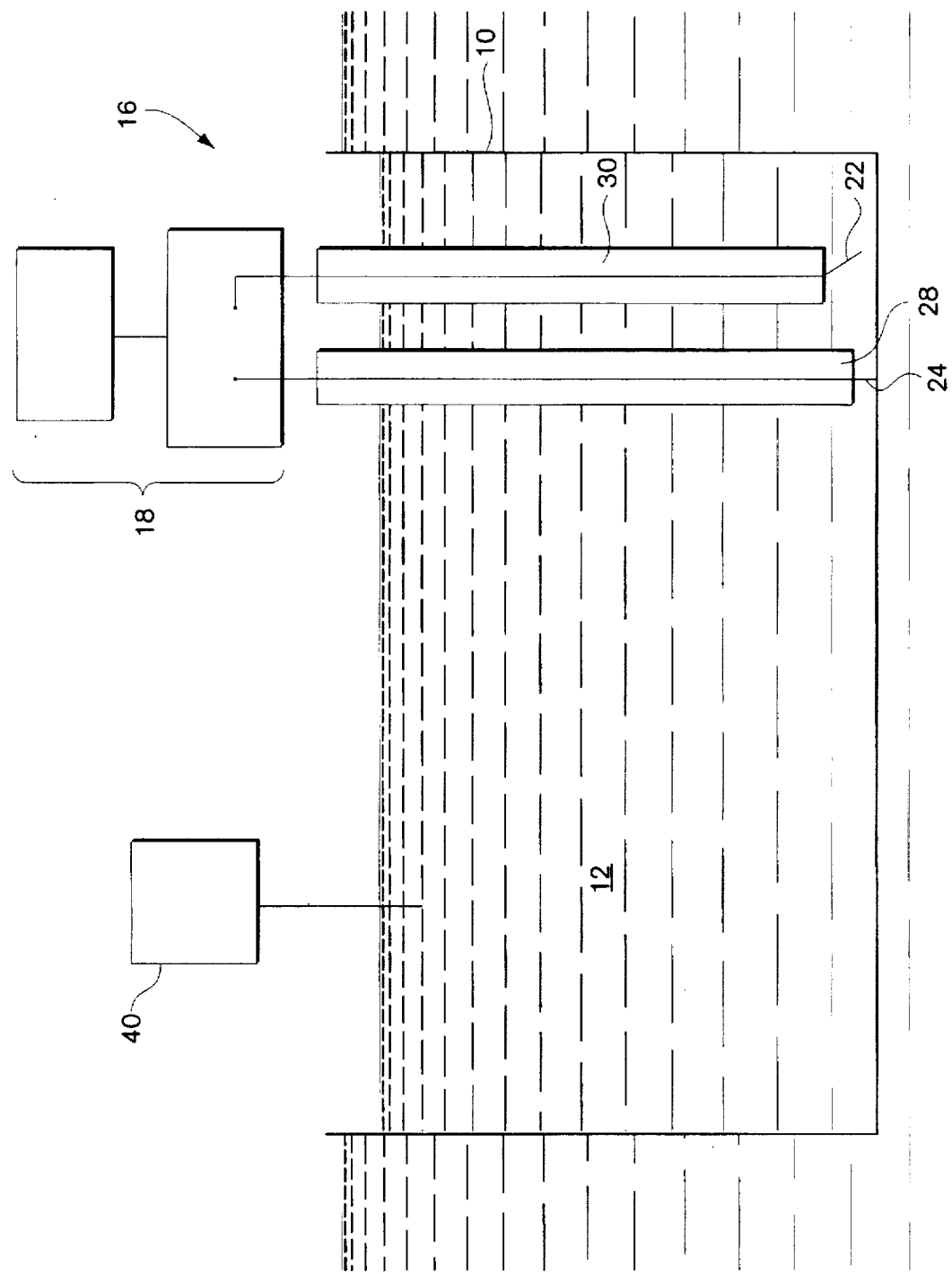
FIG. 5 is a schematic representation of an embodiment of an electrode system that does not include a reference electrode according to the present invention.

Under certain circumstances, it may be desirable to monitor only the effect of external electrical or magnetic influences on metallic material 10 without considering corrosion induced only by electrolyte 12 or establishing a potential relative to reference electrode 20. For such instances, as depicted in FIG. 5 in which elements are represented by the same reference numbers as described above, electrode system 16 need not include reference electrode 20 or cover 26.

The following example is illustrative of one embodiment of the present invention and should not be interpreted as limiting.

Example 1

A storage tank formed from type 2205 stainless steel of a sea-going vessel was partially filled with concentrated sulfuric acid. The vessel traveled through the Atlantic Ocean along the eastern seaboard of the United States, and the surface potential of the storage tank was monitored using an electrode system in accordance with the present invention. The floating electrode, shaped into a rod having a diameter of approximately 0.2 inches and a length of approximately 4 inches, was formed from the same type 2205 stainless steel as the storage tank. The floating electrode had an approximately 0.05 inch connector hole at one end. The tank electrode, formed from the same type 2205 stainless steel as the storage tank, was rod-like in shape with a diameter of approximately 0.2 inches and a length of approximately 4 inches. The tank electrode had an approximately 0.05 inch connector hole at one end and a thread designed to mate the storage tank at the other end. The reference electrode was made of high purity platinum (99.9+%) shaped into a rod having a diameter of approximately 0.12 inches and a length of approximately 4 inches. The reference electrode had an approximately 0.05 inch hole at one end.

The electrodes were each partially isolated from the sulfuric acid by PFA Swagelock tube fittings formed from Teflon. The seal on the electrode was established with one end of a regular union or a reducing union fitting. The other end of the union was mated with 0.25 inch Swagelock Teflon tubing. This tubing prevented the sulfuric acid from interacting with 22 gauge Teflon coated copper wire used to connect each electrode to the electronic measuring equipment. For each electrode, the copper lead was mechanically fixed by wrapping the lead around the electrode and passing the lead through the hole in the electrode end. For each electrode, the connection was then soldered to assure good electrical continuity.

Electronic measurements were made manually with a high impedance millivolt meter (Model No. LC4, purchased from M. C. Miller, located at Ringwood, N.J. 07456) or automatically with a high impedance data logger (Model 21X from Campbell Scientific Inc., located in Logan, Utah 84321). A data logging interval of approximately 1 minute was used. The data was recorded and stored in storage modules (Model SM716 from Campbell Scientific Inc., located in Logan, Utah 84321). Data collection from the storage modules was performed on a 486-66 personal computer using the PC208 software package (Campbell Scientific Inc., located in Logan, Utah 84321). The data was reduced and displayed using the ID2000 software package (Campbell Scientific Inc., located in Logan, Utah 84321).

FIGS. 6A–6C are graphs showing the potential, as a function of time, between the tank and reference electrode, tank and floating electrode and reference electrodes and floating electrode, respectively. FIGS. 6A and 6B demonstrate an episode of corrosion as demonstrated by the relatively sharp change in potential difference in both graphs and the comparatively high correlation between the potential differences in both graphs. In contrast, FIG. 6C shows no significant potential change, and, therefore, no indication of corrosion. Based on FIGS. 6A–6C, it may be concluded that the corrosion of the tank is due to external electrical and/or magnetic influences rather than acid chemistry only.

Having thus described certain embodiments of the present invention, various alterations, modifications and improvements will readily occur to those skilled in the art. Such alterations, modifications and improvements are intended to be part of this disclosure and are intended to be within the spirit and scope of the invention. The materials employed, as well as their shapes and dimensions, may be any required. Accordingly, the foregoing description is by way of example only and is not intended as limiting. The invention is limited only as defined in the following claims and equivalence thereto.

What is claimed is:

1. An electrode system to monitor corrosion of a surface of a structure formed from a first metallic material, the electrode system comprising:

a first electrode formed of the first metallic material, the first electrode being electrically connected to the surface of the structure;

a second electrode formed of the first metallic material, the second electrode being physically isolated from the first electrode so that a first potential exists between the second electrode and the first electrode;

an electrolyte in direct physical contact with the surface of the structure and the second electrode; and a monitor constructed and arranged to monitor corrosion of the surface of the structure by measuring the first potential.

2. The electrode system according to claim 1, wherein the structure is in a shape of a container, and wherein the second electrode is disposed within the container.

3. The electrode system according to claim 1, further comprising a correcting device constructed and arranged to detect a background change in the first potential.

4. The electrode system according to claim 1, further comprising a reference electrode in direct physical contact with the electrolyte and physically isolated from the first and second electrodes so that a second potential exists between the reference electrode and the first electrode and a third potential exists between the reference electrode and the second electrode, wherein the monitor is constructed and arranged to monitor corrosion of the surface of the structure by measuring the first, second, and third potentials.

5. The electrode system according to claim 4, further comprising a correcting device constructed and arranged to detect a background change in the first potential, the second potential, and the third potential.

6. The electrode system according to claim 4, wherein the reference electrode is capable of providing a stable and reproducible potential.

7. The electrode system according to claim 6, wherein the reference electrode is formed from a second metallic material different than the first metallic material.

8. The electrode system according to claim 1, wherein the first metallic material is a stainless steel.

9. The electrode system according to claim 1, wherein the first metallic material is copper.

10. An electrode system to monitor corrosion of a surface of a container formed of a first metallic material different than platinum, the electrode system comprising:

a platinum electrode;

a first electrode formed from the first metallic material, the first electrode being electrically connected to the surface of the container and physically isolated from the platinum electrode so that a first potential exists between the first electrode and the platinum electrode;

a second electrode formed of the first metallic material, the second electrode being physically isolated from the platinum electrode and the first electrode so that a second potential exists between the second electrode and the platinum electrode and a third potential exists between the second electrode and the first electrode;

an electrolytic solution contacting the surface of the container, the platinum electrode, and the second electrode; and a monitor constructed and arranged to monitor corrosion of the surface of the container by measuring the first potential, the second potential, and the third potential.

11. The electrode system according to claim 10, wherein the first metallic material is copper.

12. The electrode system according to claim 10, wherein the first metallic material is a corrosion resistant stainless steel.

13. The electrode system according to claim 10, wherein the first metallic material is type 2205 stainless steel.

14. The electrode system according to claim 10, further comprising a protective cover disposed adjacent to an electrode selected from the group consisting of the platinum electrode, the first electrode, and the second electrode.

15. The electrode system according to claim 10, further comprising a correcting device constructed and arranged to detect a background change in the first potential, the second potential, and the third potential.

16. The electrode system according to claim 10, wherein the container is a type 2205 stainless steel tank of a ship and the electrolytic solution is concentrated sulfuric acid.

17. The electrode system according to claim 10, wherein the container is a copper tube and the electrolytic solution is tap water.

18. A method of monitoring corrosion associated with a surface of a structure formed of a first metallic material and an electrolytic solution contacting the surface of the structure, the method comprising the steps of:

electrically connecting a first electrode to the surface of the structure, which first electrode is formed of said first metallic material for at least the areas thereof in contact with said electrolyte;

physically contacting a second electrode formed of the first metallic material with the electrolytic solution, the second electrode being physically isolated from the first electrode;

physically contacting a third electrode formed of a second metallic material with the electrolytic solution, the third electrode being physically isolated from the first electrode and the second electrode;

measuring a first potential between two electrodes selected from the group consisting of the first electrode, the second electrode and the third electrode; and measuring a second potential between two electrodes selected from the group consisting of the first electrode, the second electrode and the third electrode, the second potential being different than the first potential.

19. The method according to claim 18, further comprising a step of measuring a third potential between two electrodes selected from the group consisting of the first electrode, the second electrode, and the third electrode, the third potential being different than the first potential, the third potential being different than the second potential.

20. The method according to claim 18, further comprising a step of removing a background change in at least one potential selected from the group consisting of the first potential and the second potential.

* * * * *